United States Patent [19]

Uchikawa

[11] Patent Number: 4,731,257
[45] Date of Patent: Mar. 15, 1988

[54] PROCESS FOR PRODUCING A TEMPERATURE AND MOISTURE SENSITIVE ELEMENT

[75] Inventor: Fusaoki Uchikawa, Itami, Japan

[73] Assignee: Mitsubishi Denki Kabushiki Kaisha, Tokyo, Japan

[21] Appl. No.: 800,024

[22] Filed: Nov. 20, 1985

[30] Foreign Application Priority Data

Dec. 20, 1984 [JP] Japan .................... 59-268961
Dec. 20, 1984 [JP] Japan .................... 59-268963

[51] Int. Cl.⁴ .................................. B05D 5/12
[52] U.S. Cl. ......................... 427/122; 427/123; 427/126.3; 427/261; 427/287; 427/333; 427/379; 427/380; 427/387; 427/404; 427/407.1; 427/419.2
[58] Field of Search ............. 427/126.3, 122, 123, 427/387, 261, 379, 380, 287, 406, 407, 419.2, 333; 428/913

[56] References Cited

U.S. PATENT DOCUMENTS

| | | | |
|---|---|---|---|
| Re. 31,388 | 9/1983 | Helier et al. ............... | 427/387 |
| 2,976,188 | 3/1961 | Kohl ............................ | 428/913 |
| 3,336,119 | 8/1967 | Alban et al. ................ | 428/913 |
| 3,946,427 | 3/1976 | Iwasawa et al. ........... | 427/387 |
| 3,965,280 | 6/1976 | Ceyzerigt et al. ......... | 427/387 |
| 4,319,485 | 3/1982 | Terady et al. ............. | 73/336 |
| 4,386,336 | 5/1983 | Kinomoto et al. ......... | 338/35 |

*Primary Examiner*—Janyce A. Bell
*Attorney, Agent, or Firm*—Oblon, Fisher, Spivak, McClelland & Maier

[57] ABSTRACT

A process for producing a temperature and moisture sensitive element, which comprises a step of forming a first coating layer by applying a composition comprising a polymerized organo-silicon compound and an inorganic material onto a substrate, a step of forming a second coating layer apart from the first coating layer by applying the same composition as defined above onto the substrate, a step of heat-treating the first coating layer to form a moisture sensitive section, and a step of treating the second coating layer to form a temperature sensitive section by a treatment different from the heat treatment of the first coating layer.

8 Claims, 24 Drawing Figures

(a)

5    6    5

(b)

10  5    6    11  5

(c)

(d)

PROCESS FOR PRODUCING A TEMPERATURE AND MOISTURE SENSITIVE ELEMENT

The present invention relates to a process for producing a temperature and moisture sensitive element. More particularly, the present invention relates to a process for producing a temperature and moisture senstive element to be employed for measuring the temperature and moisture in an air conditioner, a cocking device or a dryer, whereby the temperature and moisture of an atmosphere are measured by utilizing changes in the electrical resistances.

Heretofore, as temperature and moisture senstive elements, there have been known, for instance, elements described in Japanese Unexamined Utility Model Publication No. 119559/1981 and Japanese Unexamined Pat. Publication No. 91101/1980. The former, as shown in FIG. 16 by the cross-sectional view, has a temperature sensitive element and a moisture sensitive element formed with moisture sensitive sections on one side of a substrate, and the temperature sensitive element is located adjacent to the other side of the substrate, whereby the temperature and moisture are measured by the respective elements. In the Figure, reference numeral 1 indicates the temperature sensitive element, numeral 2 indicates the moisture sensitive element, numeral 2a indicates the substrate, numeral 2b indicates a moisture sensitive section, numeral 3 indicates a wire netting which protects the temperature sensitive element 1 and the moisture sensitive element 2. The latter, as shown in FIG. 17 by the perspective view, comprises a dielectric which shows dependence of impedance upon a temperature and depedence of impedance upon a moisture, whereby signals of the temperature and moisture are detected by the surface of electrodes of the dielectric. In the Figure, reference numeral 4 indicates the dielectric and numerals 5 indicate electrodes.

As the former is a combination of two elements for a temperature sensitive element and a moisture sensitive element, there are problems that its production is complicated and that it is bulky. Further, the latter has a problem that if only impedance (resistance) is measured, it is obscure whether a change in impedance is caused by a change in temperature or moisture.

The present invention has been accomplished to solve the above-mentioned problems, and it is an object of the present invention to produce a temperature and moisture sensitive element under excellent efficiency of operation, which can exactly measure a temperature and a moisture individually, and yet which is small-sized.

The present invention provides a process for producing a temperature and moisture sensitive element, which comprises a step of forming a first coating layer by applying a composition comprising a polymerized organo-silicon compound and an inorganic material onto a substrate, a step of forming a second coating layer apart from the first coating layer by applying the same composition as defined above onto the substrate, a step of heat-treating the first coating layer to form a moisture sensitive section, and a step of treating the second coating layer to form a temperature sensitive section by a treatment different from the heat treatment of the first coating layer.

In the present invention, a temperature is measured by the temperature sensitive section and a moisture is measured by the moisture sensitive section independently, whereby both the temperature and moisture are precisely measured. Further, in the present invention, it is possible that the identical compositions are merely subjected to different treatments to form the temperature sensitive section and the moisture sensitive section so that a producing process is simplified, whereby efficiency of operation becomes excellent.

Throughout the Figures, the same reference numerals indicate the same or corresponding parts.

In the following, the present invention will be described in detail.

Figure 1:
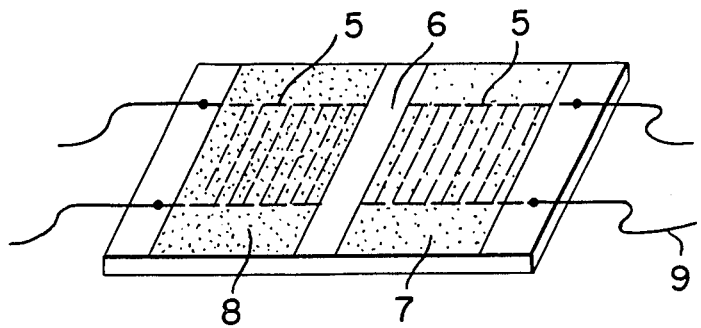
FIG. 1 is a perspective view of a temperature and moisture senstivie element in Examples 1, 3, 4, 5 and 6 of the present invention.
Figure 2:
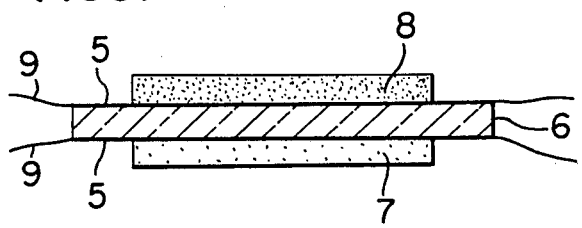
FIG. 2 is a sectional view of a temperature and moisture sensitive element in Example 2 of the present invention.

In FIGS. 1 and 2 showing an embodiment of the present invention, a temperature sensitive section 8 has characteristics that an electrical resistance varies depending upon the temperature of an atmosphere, and the moisture sensitive section 7 has characteristics that an electrical resistance varies depending upon the moisture of an atmosphere, these changes in electrical resistance are measured by the electrodes 5, whereby the temperature and moisture are measured individually.

Now, the present invention will be described in detail with reference to Examples. However, it should be understood that the present invention is by no means restricted by these specific Examples.

EXAMPLE 1

Figure 3:
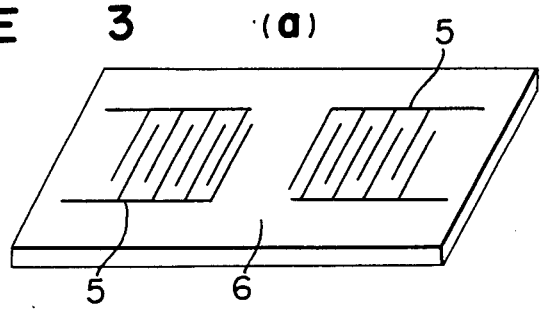
FIG. 3 is a perspective view showing the sequence of the steps of the Examples 1, 3 and 4 of the present invention.
Figure 3:
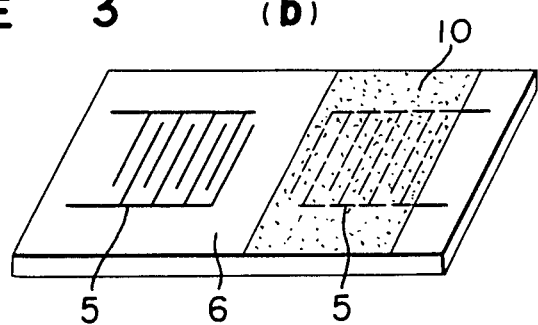
Figure 3:
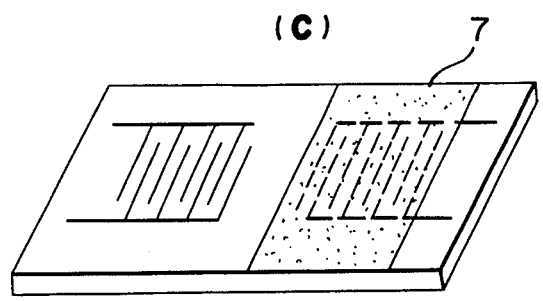
Figure 3:
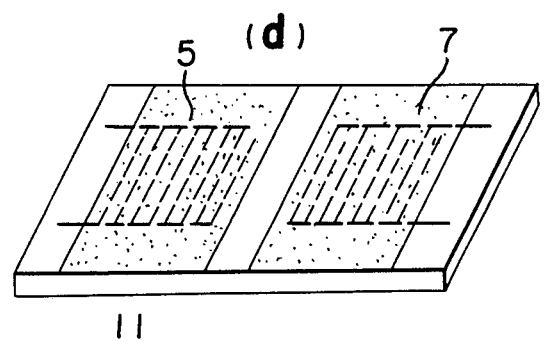
Figure 3:
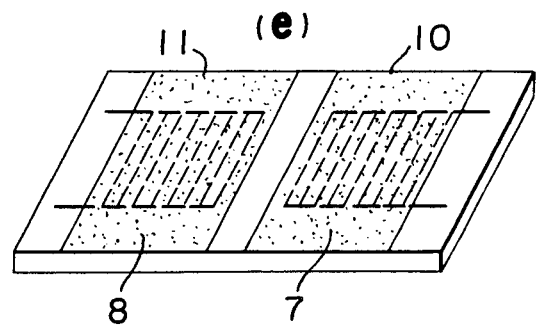

FIG. 3 is a perspective view showing the sequence of the steps of the Examples 1, 3 and 4 of the present invention. In the Figure, reference numeral 10 indicates a first coating layer, and numeral 11 indicates a second coating layer.

On the same surface of an alumina substrate 6, two pairs of comb-shaped opposed electrodes 5 made of Ag paste were formed apart from each other [FIG. 3(a)]. A thinner was added to Composition 1 indicated below; the mixture was stirred with a stirrer, and then the stirred mixture was applied onto one of the two pairs of the electrodes in a thickness of about 50 μm by brush coating to form the first coating layer 10 [FIG. 3(b)]. The first coating layer was subjected to a heat treatment (in this case: firing) at 500° C. for 1.5 hours to provide it with moisture sensitive function, whereby a moisture sensitive section 7 was formed [FIG. 3(c)]. In the next place, the above-mentioned stirred mixture was applied onto another pair of the electrodes 5 in a thickness of about 50 μm by brush coating to form the second coating layer [FIG. 3(d)]. The second coating layer was subjected to heat treatment (in this case: firing) at 250° C. for 40 minutes to provide the second coating layer with temperature sensitive function, whereby a temperature sensitive section 8 was formed [FIG. 3(e)]. A Cu lead wire was bonded to each of the two pairs of the opposed electrodes to prepare a temperature and moisture sensitive element (FIG. 1).

| Composition 1 | |
|---|---|
| Polymerized organo-silicon compound: methylphenyl silicone prepolymer | 62.6% by weight |
| Inorganic materials: | |
| $Fe_3O_4$ | 19.4% by weight |
| $Li_2O$ | 8.7% by weight |
| Additive: $SiO_2$ | 9.3% by weight |

Figure 4:
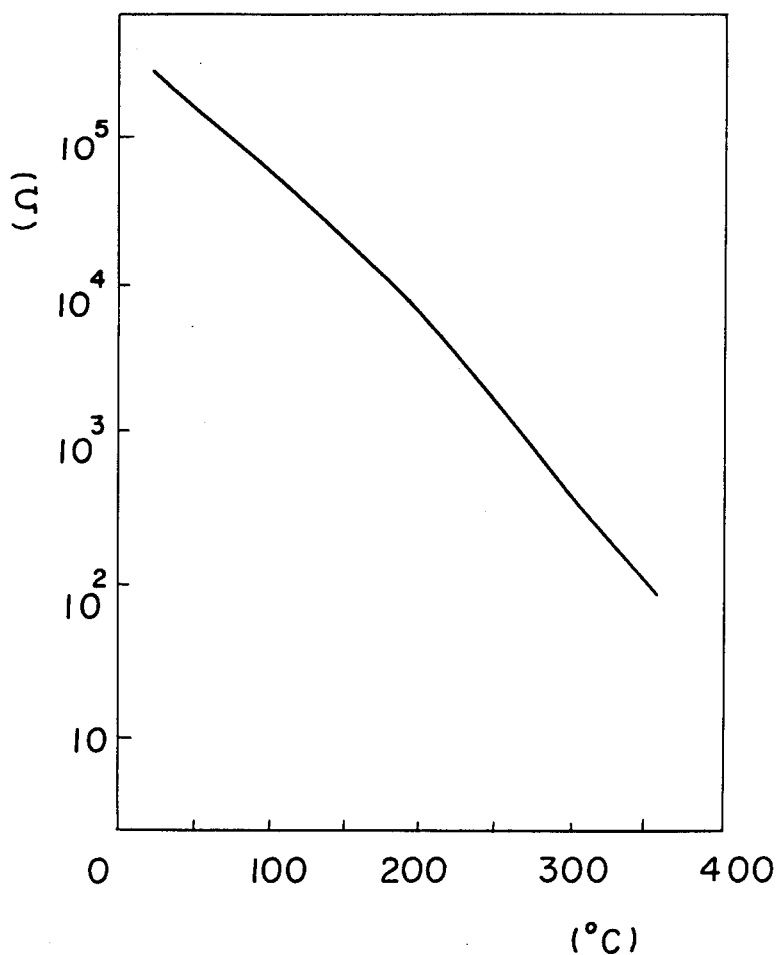
FIG. 4 is a graph showing temperature sensitive characteristics of the temperature and moisture sensitive element in Example 1 of the present invention.
Figure 5:
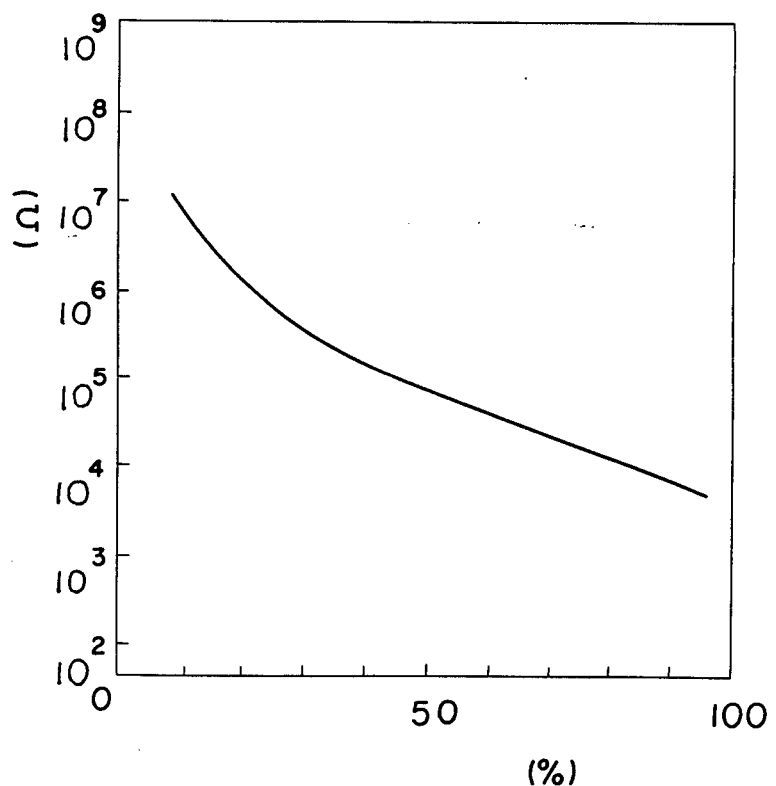
FIG. 5 is a graph showing moisture sensitive characteristics of the same element.
Figure 6:
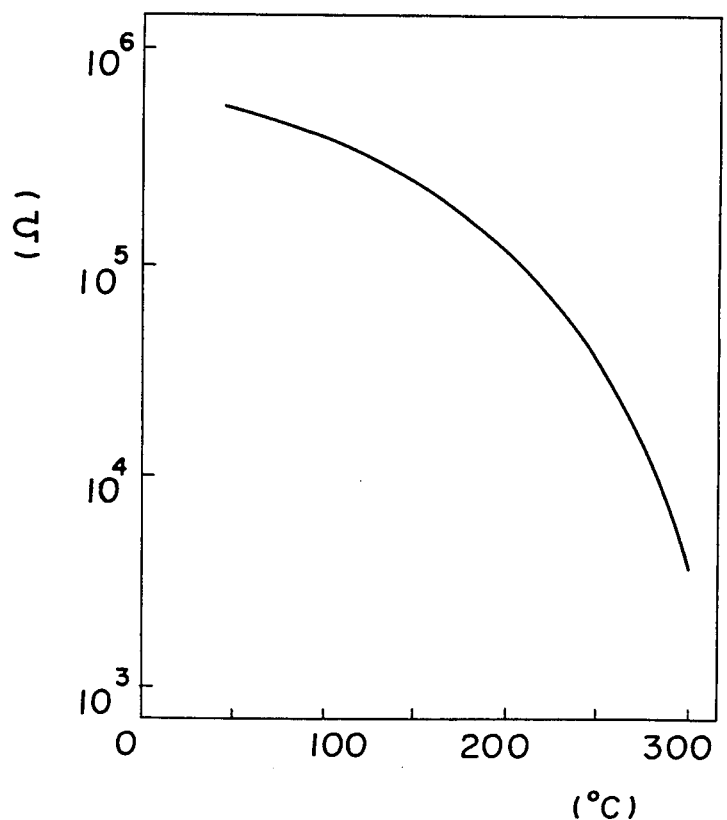
FIG. 6 is a graph showing temperature sensitive characteristics of the temperature and moisture sensitive element in Example 2 of the present invention.
Figure 7:
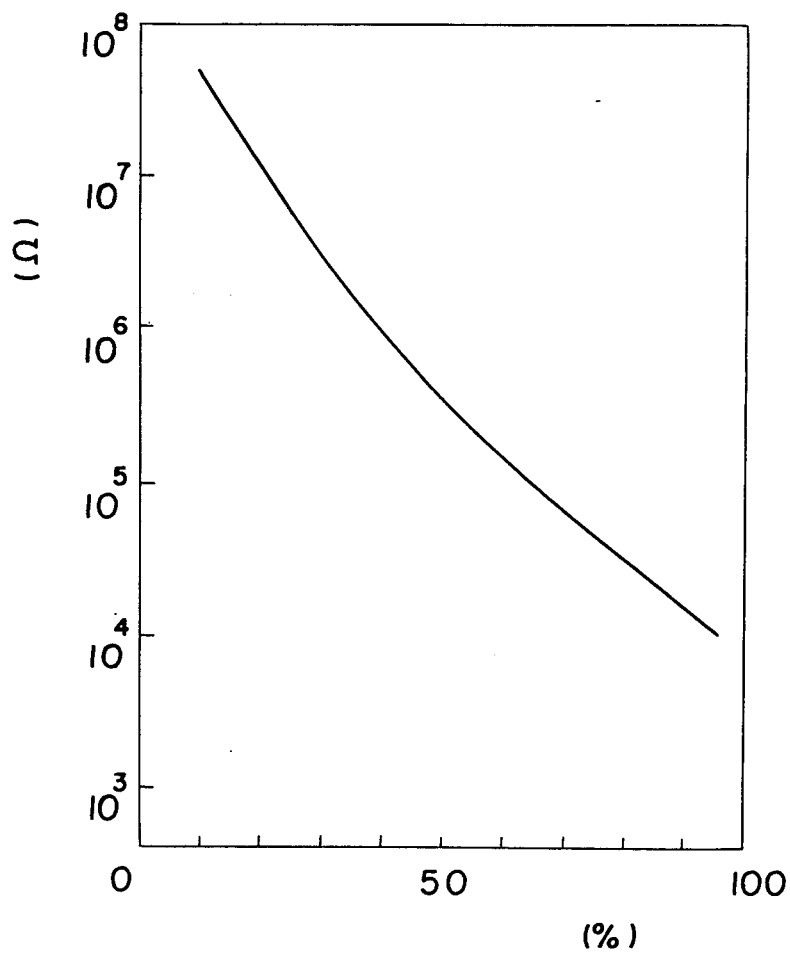
FIG. 7 is a graph showing moisture sensitive characteristics of the same element.

FIG. 4 is a graph showing temperature sensitive characteristics of the temperature sensitive section 8 thus obtained. Further, the temperature sensitive section 8 shows no substantial depedence of impedance upon a moisture so that there is no practical problem. FIG. 5 is a graph showing moisture sensitive characteristics of the moisture sensitive section 7 of the same element. Further, the moisture sensitive section 7 shows no substantial dependence of impedance upon a temperature so that there is no practical problem. Thus, the element shows both excellent temperature sensitive characteristics and moisture sensitive characteristics.

EXAMPLE 2

On the both side of an alumina substrate 6, comb-shaped opposed electrodes made of Pt-Au paste were formed, respectively, and a Pt lead wire was bonded to each of the electrodes. A thinner was added to Composition 2 indicated below, the mixture was stirred with a stirrer, then the stirred mixture was filmily applied onto the two pairs of the opposed electrodes in a thickness of about 40 μm by dipping treatment to form a first and second coating layer. The second coating layer was shielded with a heat insulator to intercept a heat, the first coating layer was subjected to heat treatment (in this case: firing) at 500° C. for 1.5 hours to provide it with moisture sensitive function, whereby a moisture sensitive section 7 was formed. The heat insulator which shielded the second coating layer was removed, and the second layer was subjected to heat treatment (in this case: firing) at 300° C. for 40 minutes to provide it with temperature sensitive function, whereby a temperature sensitive section 8 was formed. Thus, a temperature and moisture sensitive element was obtained.

| Composition 2 | |
|---|---|
| Polymerized organo-silicon compound: methyl silicone prepolymer | 42.7% by weight |
| Inorganic materials: | |
| $BaTiO_3$ | 27.3% by weight |
| NiO | 23.1% by weight |
| Additive: Bentonite | 6.9% by weight |

The temperature and moisture sensitive element shows similar temperature sensitive characteristics and moisture sensitive characteristics to those of the element in Example 1.

EXAMPLE 3

A temperature and moisture sensitive element of the present invention was prepared in accordance with the process of FIG. 3. Namely, on the same surface of an alumina substrate, two pairs of comb-shaped opposed electrodes made of Pt-Pd paste were formed apart from each other. A thinner was added to Composition 3 indicated below, the mixture was stirred with a stirrer, then the stirred mixture was applied onto one of the two pairs of the electrodes in a thickness of about 20 μm by brush coating to form the first coating layer. The first coating layer was subjected to heat treatment at 560° C. for 2 hours to provide it with moisture sensitive function, whereby a moisture sensitive section was formed. In the next place, the same stirred mixture as mentioned above was applied onto the other pair of the electrodes in a thickness of about 20 μm by brush coating to form the second coating layer. The second layer was subjected to heat treatment at 300° C. for 1 hour to provide it with temperature sensitive function, whereby a temperature sensitive section was formed. A lead wire was bonded to each electrode to prepare a temperature and moisture sensitive element.

| Composition 3 | |
|---|---|
| Polymerized organo-silicon compound: methylphenyl silicone | 37.5% by weight |
| Inorganic materials: | |
| Se | 30.8% by weight |
| Zn | 25.9% by weight |
| Additive: Talc | 5.8% by weight |

Figure 8:
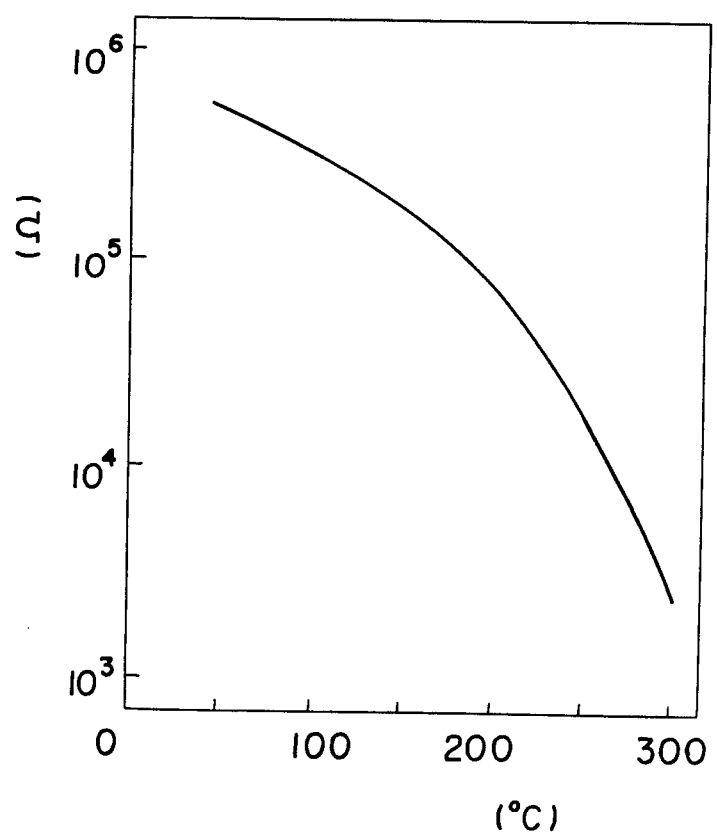
FIG. 8 is a graph showing temperature sensitive characteristics of the temperature and moisture sensitive element in Example 3 of the present invention.
Figure 9:
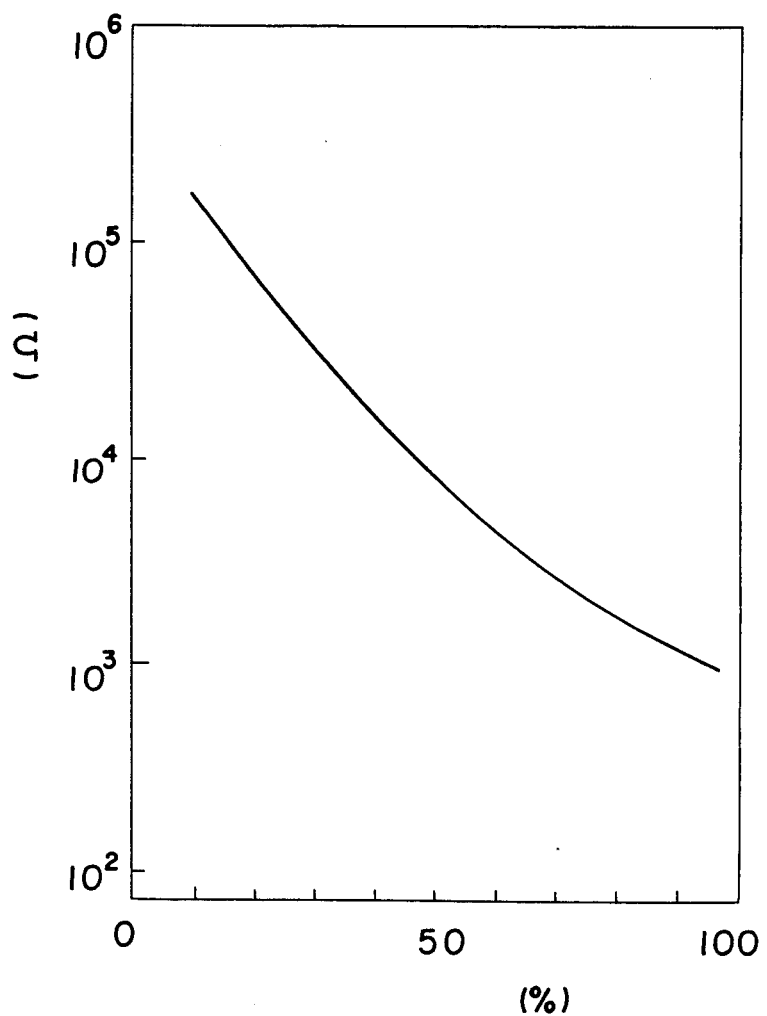
FIG. 9 is a graph showing moisture sensitive characteristics of the same element.

FIG. 8 is a graph showing temperature sensitive characteristics of the temperature sensitive section thus obtained. As dependence of impedance upon a moisture of the temperature sensitive section is at most 6% as a change in electrical resistance relative to a change in relative humidity from 10 to 95%, there is no practical problem. FIG. 9 is a graph showing moisture sensitive characteristics of the moisture sensitive section. As a depedence of impedance upon a temperature of the moisture sensitive section is at most 4% as a change in electrical resistance relative to a change of 10° C. in the temperature, there is no practical problem. Thus, the elements shows both excellent temperature sensitive characteristics and moisture sensitive characteristics.

EXAMPLE 4

A temperature and moisture sensitive element of the present invention was prepared in accordance with the process of FIG. 3. Namely, on the same surface of an alumina substrate, two pairs of comb-shaped opposed electrodes made of Pt-Pd paste were formed apart from each other. A thinner was added to Composition 4 indicated below, the mixture was stirred with a stirrer, then the stirred mixture was applied onto one of the two pairs of the electrodes in a thickness of about 30 μm by brush coating to form the first coating layer. The first coating layer was subjected to heat treatment at 600° C. for 1 hour to provide it with moisture sensitive function, whereby a moisture sensitive section was formed. In the next place, the same stirred mixture as mentioned above was applied onto another pair of the electrodes in the thickness of about 30 μm by brush coating to form the second coating layer. The second coating layer was subjected to heat treatment at 320° C. for 1 hour to provide it with temperature sensitive function, whereby a temperature sensitive section was formed. A lead wire was bonded to each electrode to prepare a temperature and moisture sensitive element.

| Composition 4 | |
|---|---|
| Polymerized organo-silicon compound: epoxy-modified silicone | 41.5% by weight |
| Inorganic material: | |
| FeSb | 28.6% by weight |
| Graphite | 17.3% by weight |
| Additives: | |
| $Al_2O_3$ | 8.9% by weight |
| Mica | 3.7% by weight |

Figure 10:
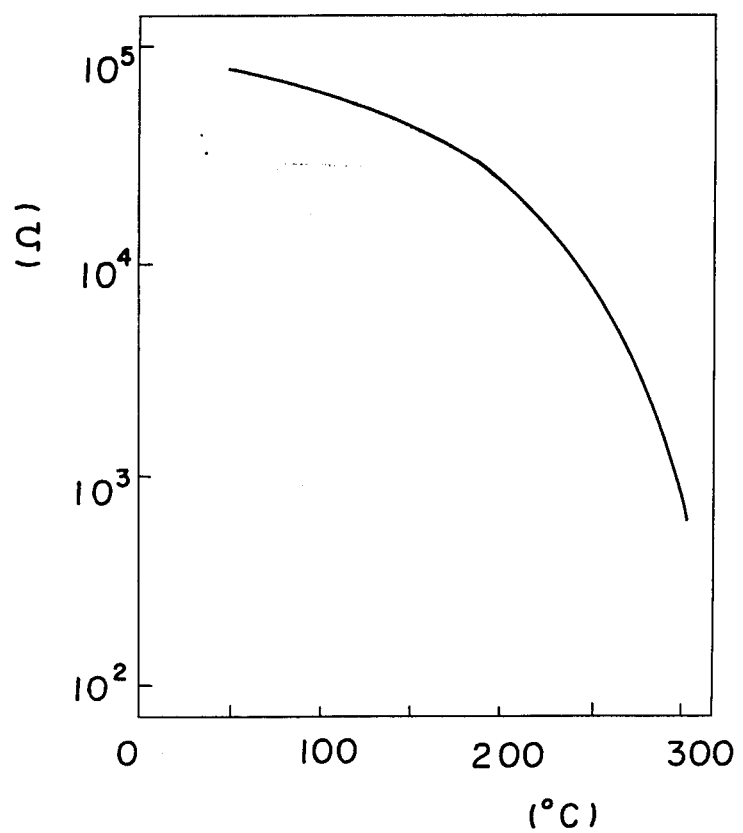
FIG. 10 is a graph showing temperature sensitive characteristics of the temperature and moisture sensitive element in Example 4 of the present invention.
Figure 11:
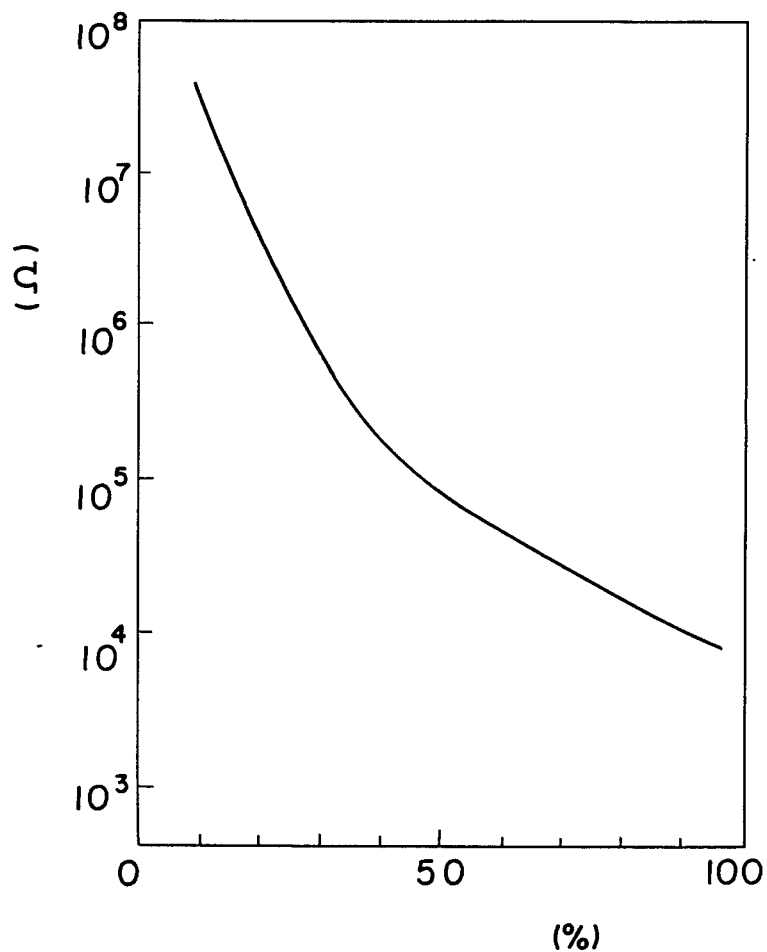
FIG. 11 is a graph showing moisture sensitive characteristics of the same element.

FIG. 10 is a graph showing temperature sensitive characteristics of the temperature sensitive section. As dependence of impedance upon a moisture of the temperature sensitive section is at most 8% as a change in electrical resistance relative to a change in relative humidity from 10 to 95%, there is no practical problem. FIG. 11 is a graph showing moisture sensitive characteristics of the moisture sensitive section. As dependence of impedance upon a temperature of the moisture sensitive section is at most 5% as a change in electrical resistance relative to a change of 10° C. in a temperature, there is no practical problem. Thus, the element has both excellent temperature sensitive characteristics and moisture sensitive characteristics.

The present invention is by no means restricted by the above-mentioned specific Examples. Accordingly, the temperature sensitive section may be formed prior to a formation of the moisture sensitive section, for instance, the first and the second coating layers are formed on electrodes at a time by spray coating, heat treatments are conducted almost simultaneously by the laser irradiations with different quantities of irradiation energy, whereby it is possible to shorten and operation time.

As a polymerized organo-silicon compound of the present invention, there may be employed, for instance, greasy, varnish-like or oily prepolymer of organo-siloxane such as methylphenyl silicone or methyl silicone, or modified type silicone such as epoxy-modified, acryl-modified or urethane-modified silicone.

As an inorganic material of the present invention, a metal oxide such as $Fe_3O_4$, $Li_2O$, $TiO_2$, $SiO_2$ or NiO, a compound oxide such as $BaTiO_3$, a powder of metal such as Al, Cu, Ni or Zn, a powder of alloy such as FeSb a powder of carbon such as graphite and a powder of non-metal such as selenium.

The composition of the present invention may contain a powder of inorganic material such as a metal oxide as an additive for the purposes of the improvement of coat-forming effect, the acceleration of drying and curing, the prevention of cracking and the improvement of bonding performance to the substrate. As an additive, there may be mentioned $SiO_2$, $Al_2O_3$, bentonite, mica or talc.

As ways applying the first coating layer and second coating layers, there may be employed brush coating, spray coating or dipping treatment.

The temperature of heat treatment of the second coating layer for formation of the temperature sensitive section varies depending upon a state of the polymerized organo-silicon compound (molecular weight, a type of organic group) or upon an atmosphere of heat treatment. However, the temperature is desirably at most a temperature at which an organic group contained in the polymer would not completely be resolved, i.e. at most about 450° C. is desired. The temperature sensitive section may also be formed by heat-treating the second coating layer at a temperature of at least 800° C. in which the polymer is completely resolved and sintered so that it becomes non-porous to lose its moisture sensitive function.

A temperature of heat treatment of the first coating layer for formation of the moisture sensitive section is desirably from about 500° to 700° C. at which the coating layer becomes porous to increase its moisture sensitivity.

EXAMPLE 5

Figure 12:
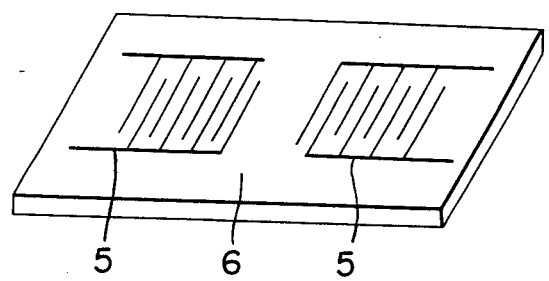
FIG. 12 is a perspective view showing the sequence of the steps in Examples 5 and 6 of the present invention.
Figure 12:
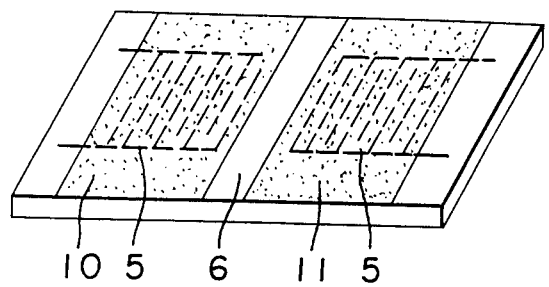
Figure 12:
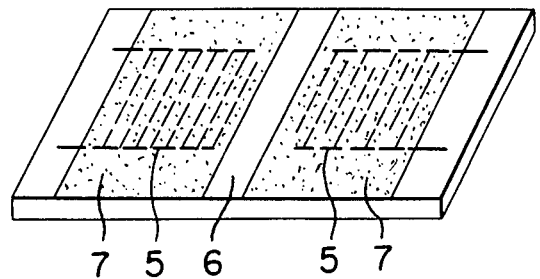
Figure 12:
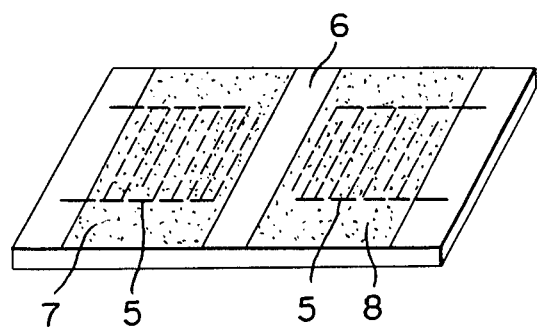

FIG. 12 is a perspective view showing the sequence of the steps of Examples 5 and 6 of the present invention.

In the Figure, reference numeral 10 indicates a first coating layer, and numeral 11 indicates a second coating layer. On the same surface of an alumina substrate 6, two pairs of comb-shaped opposed electrodes 5 made of Ag paste were formed apart from each other [FIG. 12 (a)]. A thinner was added to Composition 5 indicated below; the mixture was stirred with a stirrer, and then the stirred mixture was applied onto the two pairs of opposed electrodes 5 in a thickness of about 50 μm by brush coating to form the first and second coating layers 10, 11 [FIG. 12 (b)]. The first and the second coating layers were fired at 480° C. for 2 hours to form moisture sensitive sections [FIG. 12 (c)]. A fluorine-containing resin was applied in a thickness of 4.5 μm as a coating material onto the surface of the second coating layer as the moisture sensitive section thus formed to form a temperature sensitive section [FIG. 12 (d)]. The moisture sensitive section is rendered water repellent and non-porous by applying a coating material so that it will not show moisture sensitive properties, whereby it can be used as a temperature sensitive section. A Cu lead wire was bonded to each of the two pairs of the opposed electrodes to prepare a temperature and moisture sensitive element.

| Composition 5 | |
|---|---|
| Polymerized organo-silicon compound: methylphenyl silicon prepolymer | 35.4% by weight |
| Inorganic materials: | |

| -continued | |
|---|---|
| Composition 5 | |
| TiO$_2$ | 60.6% by weight |
| SiO$_2$ | 4.0% by weight |

Figure 13:
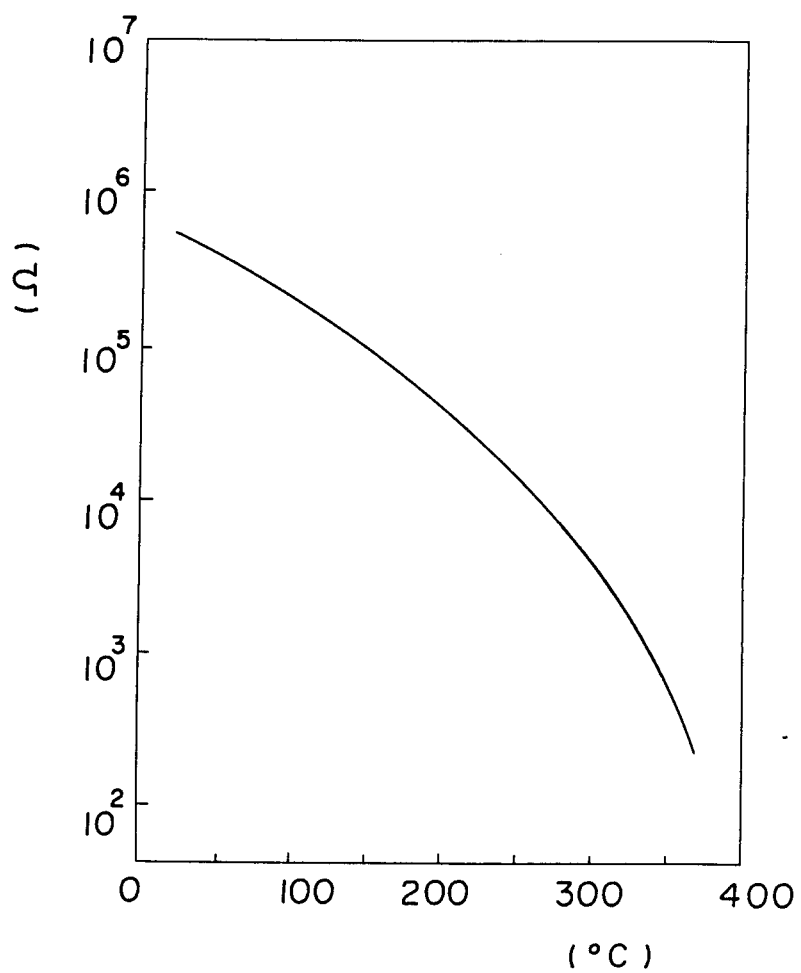
FIG. 13 is a graph showing temperature sensitive characteristics of the temperature and moisture sensitive element in Example 5 of the present invention.
Figure 14:
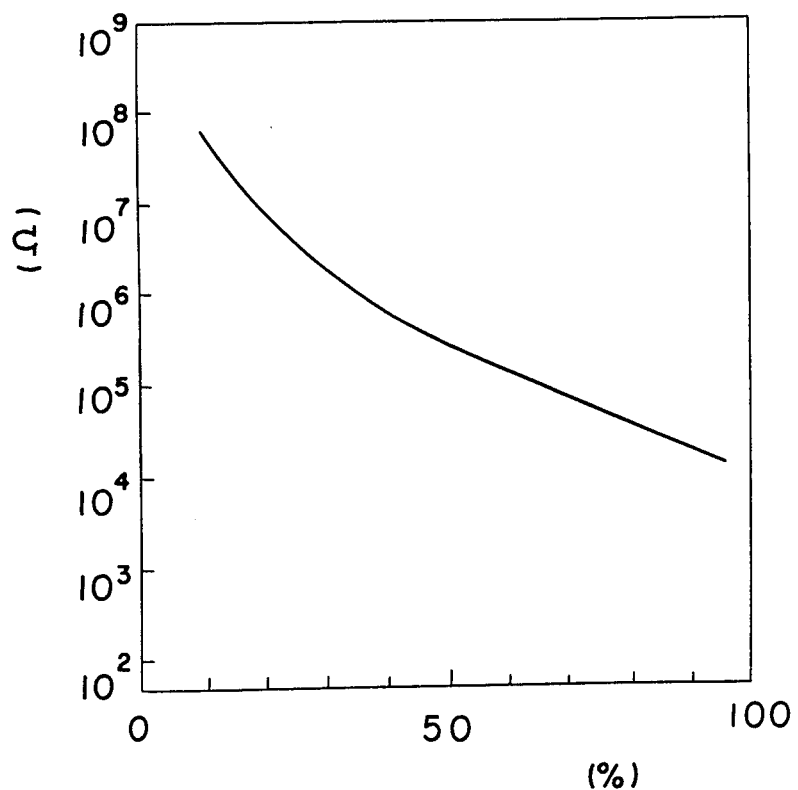
FIG. 14 is a graph showing moisture sensitive characteristics of the same element.

FIG. 13 is a graph showing temperature sensitive characteristics of the temperature sensitive section 8 thus obtained. FIG. 14 is a graph showing moisture sensitive characteristics of the moisture sensitive section 7 of the same element.

EXAMPLE 6

Figure 15:
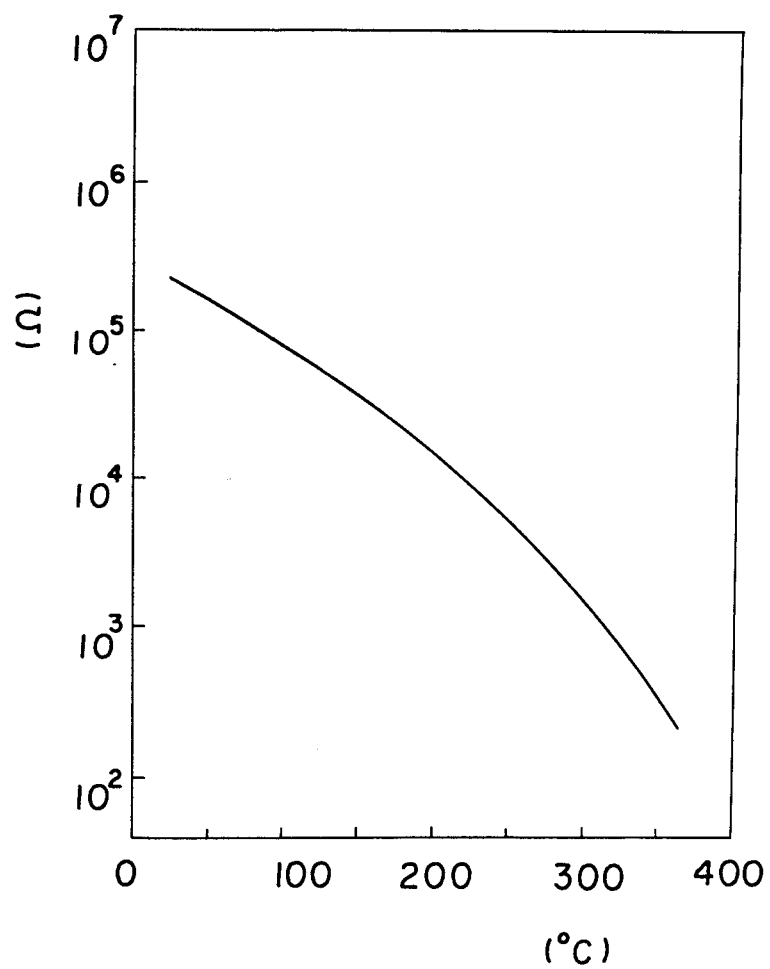
FIG. 15 is a graph showing temperature sensitive characteristics of the temperature and moisture sensitive element in Example 6 of the present invention.
Figure 16:
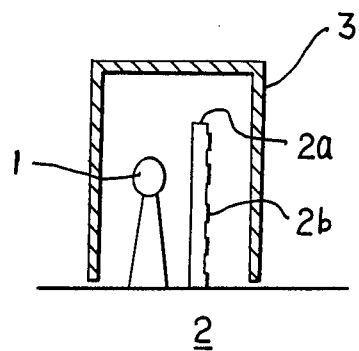
FIG. 16 is a perspective view of a conventional temperature and moisture sensitive element.
Figure 17:
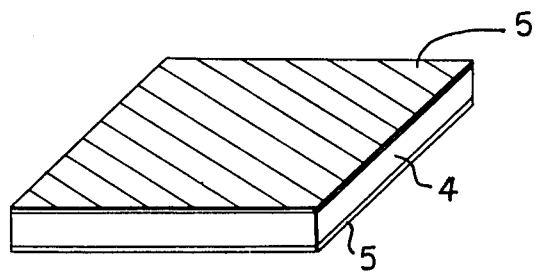
FIG. 17 is a perspective view of a conventional temperature and moisture sensitive element.

Moisture sections were formed in the same manner as in Example 5. A coating material comprising a polymerized organo-silicon compound as the principal ingredient was applied onto the surface of the second coating layer as the moisture sensitive section thus formed in a thickness of 4.5 μm to form a temperature sensitive section, whereby a temperature and moisture sensitive element was prepared. FIG. 15 is a graph showing temperature sensitive characteristics of the temperature sensitive section of this temperature and moisture sensitive element. It is evident from the Figure that the tendency of high resistance does not appear in the temperature sensitive characteristics of the temperature sensitive section formed by applying the above coating material as that in the temperature sensitive section formed by applying the fluorine-containing resin in Example 5. And its sensitivity showed no substantial reduction as compared with that of temperature sensitive section of Example 5.

A coating layer comprising a polymerized organo-silicon compound or an alkali metal silicate as the principal ingredient has a thermal conductivity whose value approximates that of the fired coating layer (the moisture sensitive section) and its sensitivity is not reduced. Further, it was confirmed that such a coating layer did not impart such high resistance as other resin type coating materials.

As a coating material of the present invention, one might use an alkali metal silicate as the principal ingredient (such as water glass), a coating material comprising a polymerized organo-silicon compound (such as silicone varnish or silicone heat-resistant coating), a high polymeric organic type resin such as a fluorine-containing resin (such as Teflon coating material or polyvinylidene fluoride type paints) or polyimide type resin. In addition, if the coating of the high polymeric organic type resin is too thick, temperature sensitive characteristics of the coating becomes poor, therefore some care should be taken to prevent coating to too high a depth.

As mentioned above, the present invention provides an effect that it is possible to produce a temperature and moisture sensitive element, which can exactly measure temperature and moisture individually, and yet which is small-sized and can be produced efficiently by the process which comprises a step of forming a first coating layer by applying a composition comprising a polymerized organo-silicon compound and an inorganic material onto a substrate, a step of forming a second coating layer apart from the first coating layer by applying the same composition as defined above onto the subsrate, a step of heat-treating the first coating layer to form a moisture sensitive section, and a step of treating the second coating layer to form a temperature sensitive section by a treatment different from the heat treatment of the first coating layer.

I claim:

1. A process for producing a temperature and moisture sensitive element, which comprises a step of forming a first coating layer by applying a composition comprising a polymerized organo-silicon compound and an inorganic material comprising at least one member selected from the group consisting of a metal oxide, a compound metal oxide, a metal powder, an alloy powder, a carbon powder and a selenium powder onto a surface of an aluminum substrate, a step of forming a second coating layer apart from the first coating layer by applying the same composition as defined above onto the same surface, a step of heat-treating the first coating layer to form a moisture sensitive section, and a step of treating the second coating layer to form a temperature sensitive section by a treatment different from the heat treatment of the first coating layer, said heat-treating of the first coating layer being at about 500° C. to about 700° C., and said treating of the second coating layer being at less than about 450° C. or at more than about 800° C.

2. The process according to claim 1, wherein the first coating layer and the second coating layer are formed simultaneously.

3. The process according to claim 1, wherein the first coating layer and the second coating layer are formed sequentially.

4. The process according to claim 1, wherein the second coating layer is heat-treated at a temperature different from the temperature of the heat treatment of the first coating layer to form the temperature sensitive section.

5. A process for producing a temperature and moisture sensitive element, which comprises a step of forming a first coating layer by applying a composition comprising a polymerized organosilicon compound and an inorganic material comprising at least one member selected from the group consisting of a metal oxide, a compound metal oxide, a metal powder, an alloy powder, a carbon powder and a selenium powder onto a surface of an alumina substrate, a step of forming a second coating layer apart from the first coating layer by applying the same composition as defined above onto the same surface, a step of heat-treating the first coating layer to form a moisture sensitive section, and a step of treating the second coating layer to form a temperature sensitive section by a treatment different from the heat treatment of the first coating layer, wherein the first and second coating layers are subjected to the same heat treatment to renew the coating barous to form moisture sensitive sections, respectively, and a coating material which renders the second coating water repellant is applied onto the surface of the second coating layer to turn the moisture sensitive section into a temperature sensitive section.

6. The process according to claim 5, wherein the coating material is composed essentially of an alkali metal silicate.

7. The process according to claim 1, wherein the polymerized organo-silicon compound is methylphenyl silicone, methyl silicone, epoxy-modified silicone, acryl-modified silicone or urethane-modified silicone.

8. The process according to claim 1, wherein the inorganic material comprises at least one member selected from the group consisting of Fe$_3$O$_4$, Li$_2$O, TiO$_2$, SiO$_2$, NiO, BaTiO$_3$, Al, Cu, Ni, Zn, FeSb, graphite and selenium.

* * * * *